US010446015B2

(12) United States Patent
Praplan et al.

(10) Patent No.: US 10,446,015 B2
(45) Date of Patent: Oct. 15, 2019

(54) ELECTRONIC MONITORING BRACELET

(71) Applicant: GEOSATIS SA, Le Noirmont (CH)

(72) Inventors: Vincent Praplan, Le Noirmont (CH); Edmund James Colli-Vignarelli, Les Avanchets (CH); Urs Hunkeler, Vogelsang (CH); José Carlos Fernandes Demétrio, Mont-sur-Lausanne (CH)

(73) Assignee: GEOSATIS SA, Le Noirmont (CH)

( * ) Notice: Subject to any disclaimer, the term of this patent is extended or adjusted under 35 U.S.C. 154(b) by 0 days.

(21) Appl. No.: 14/367,233

(22) PCT Filed: Dec. 19, 2012

(86) PCT No.: PCT/IB2012/057490
§ 371 (c)(1),
(2) Date: Jun. 19, 2014

(87) PCT Pub. No.: WO2013/093808
PCT Pub. Date: Jun. 27, 2013

(65) Prior Publication Data

US 2015/0048939 A1 Feb. 19, 2015

(30) Foreign Application Priority Data

Dec. 20, 2011 (EP) .................................... 11194712
Dec. 20, 2011 (EP) .................................... 11194714

(51) Int. Cl.
*G08B 25/01* (2006.01)
*G07C 9/00* (2006.01)
(Continued)

(52) U.S. Cl.
CPC ........ *G08B 25/016* (2013.01); *G07C 9/00111* (2013.01); *G08B 21/0286* (2013.01);
(Continued)

(58) Field of Classification Search
CPC ........................... G07C 9/00111; G08B 21/22; G08B 21/0286; G08B 29/185; G08B 25/10;
(Continued)

(56) References Cited

U.S. PATENT DOCUMENTS 3,049,465 A 8/1962 Wilkins
4,689,612 A 8/1987 Schaal et al.
(Continued)

FOREIGN PATENT DOCUMENTS

DE 102005016425 A1 10/2006
EP 0177394 A1 4/1986
(Continued)

OTHER PUBLICATIONS

English translation of the Written Opinion of the International Searching Authority issued by the European Patent Office, dated Feb. 27, 2013, for International Application No. PCT/IB2012/057490; 7 pages.
(Continued)

*Primary Examiner* — Mirza F Alam
(74) *Attorney, Agent, or Firm* — Faegre Baker Daniels LLP

(57) ABSTRACT

An electronic monitoring bracelet, comprising a ring-shaped body (2) configured so as to be mounted around a limb or an object, and an electronic monitoring system positioned in the body, the electronic monitoring system comprising an integrity detection system (4) and an internal source of energy (12). The ring-shaped body (2) is in the form of a rigid shell containing a chamber or several chamber sections in which are positioned components of the electronic monitoring system, the ring-shaped body entirely encircling the bracelet.

34 Claims, 12 Drawing Sheets

Figure 1A:
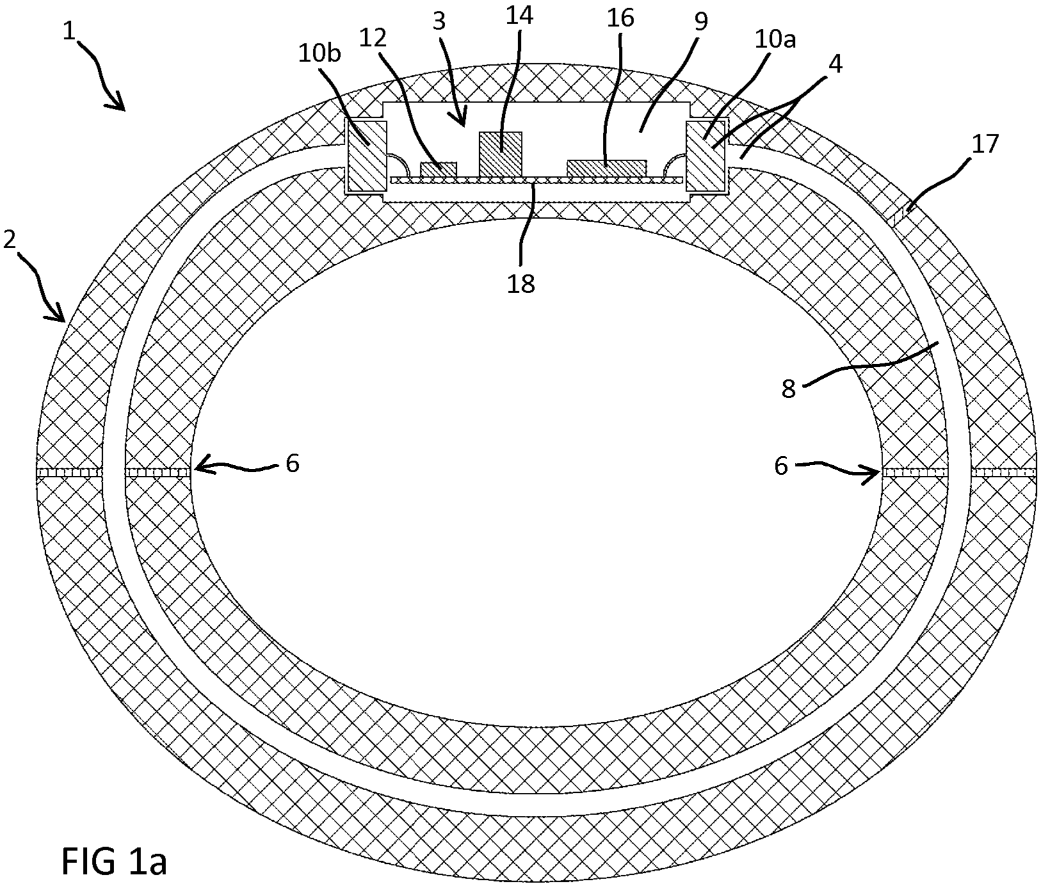

(51) Int. Cl.
*G08B 25/10* (2006.01)
*G08B 21/02* (2006.01)
*G08B 21/22* (2006.01)
*G08B 29/18* (2006.01)

(52) U.S. Cl.
CPC ......... *G08B 21/0291* (2013.01); *G08B 21/22* (2013.01); *G08B 25/10* (2013.01); *G08B 29/185* (2013.01)

(58) Field of Classification Search
CPC .............. G08B 21/0446; G08B 21/043; H04N 21/44213; H04N 21/44231
USPC ............................ 340/539.11, 539.13, 573.4
See application file for complete search history.

(56) References Cited

U.S. PATENT DOCUMENTS

| | | | | | |
|---|---|---|---|---|---|
| 6,169,494 | B1* | 1/2001 | Lopes | A61B 5/0002 | 340/8.1 |
| 2005/0068169 | A1* | 3/2005 | Copley | G08B 21/0283 | 340/539.13 |
| 2005/0240959 | A1* | 10/2005 | Kuhn | H04N 7/163 | 725/25 |
| 2008/0001764 | A1* | 1/2008 | Douglas | G07C 9/00111 | 340/573.1 |
| 2012/0138637 | A1* | 6/2012 | Ciavarella | A44C 5/0023 | 224/148.4 |
| 2013/0143519 | A1* | 6/2013 | Doezema | G08B 21/0446 | 455/404.2 |
| 2014/0139637 | A1* | 5/2014 | Mistry | H04N 5/2252 | 348/46 |
| 2015/0335284 | A1* | 11/2015 | Nuovo | A61B 5/0022 | 600/301 |

FOREIGN PATENT DOCUMENTS

| | | | |
|---|---|---|---|
| EP | 1302822 | A1 | 4/2003 |
| WO | WO8809541 | A1 | 12/1988 |
| WO | WO0059759 | A1 | 10/2000 |

OTHER PUBLICATIONS

International Preliminary Report on Patentability in the French language issued by the Bureau international de l'OMPI, Geneva, Switzerland, dated Jun. 24, 2014 for International Application No. PCT/IB2012/057490; 8 pages.
English translation of the International Preliminary Report on Patentability issued by the International Bureau of WIPO, Geneva, Switzerland, dated Jun. 24, 2014 for International Application No. PCT/IB2012/057490; 8 pages.
European Search Report issued by the European Patent Office, Munich, Germany, dated May 2, 2012, for European patent Application No. 11194712.3; 6 pages.
European Search Report issued by the European Patent Office, Munich, Germany, dated Oct. 4, 2012, for European patent Application No. 11194714.9; 7 pages.
International Search Report and Written Opinion (in French language) issued by the European Patent Office, dated 27 Feb. 2013, for related International Application No. PCT/IB2012/057490; 13 pages.
International Search Report (English language translation) issued by the European Patent Office, dated Feb. 27, 2013, for related International Application No. PCT/IB2012/057490; 3 pages.

* cited by examiner

FIG 6a
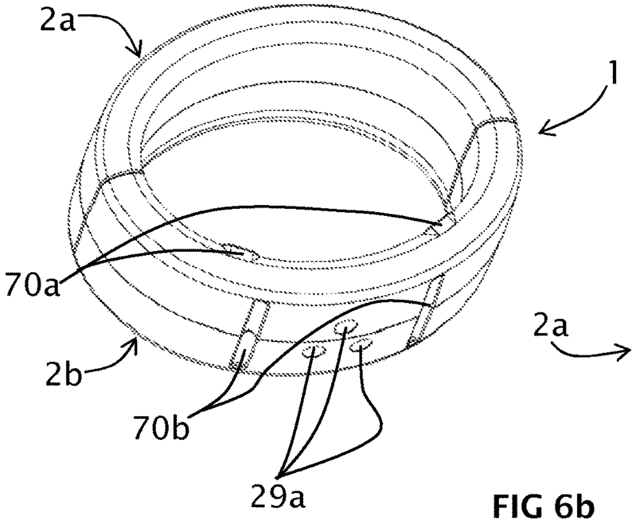
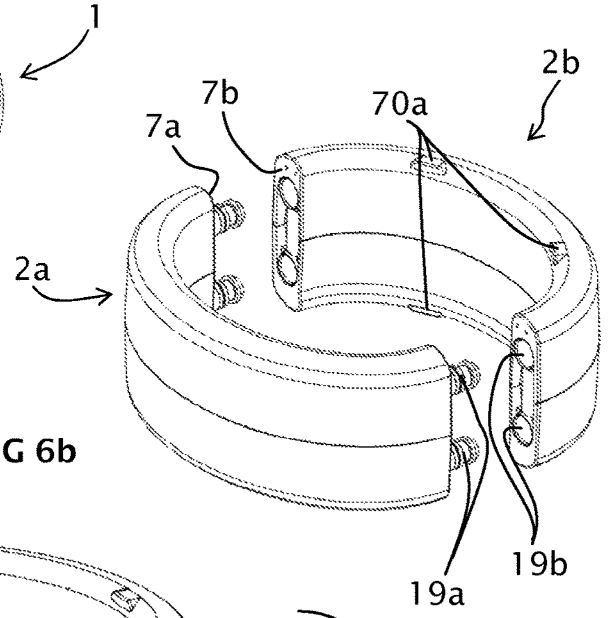
FIG 6b
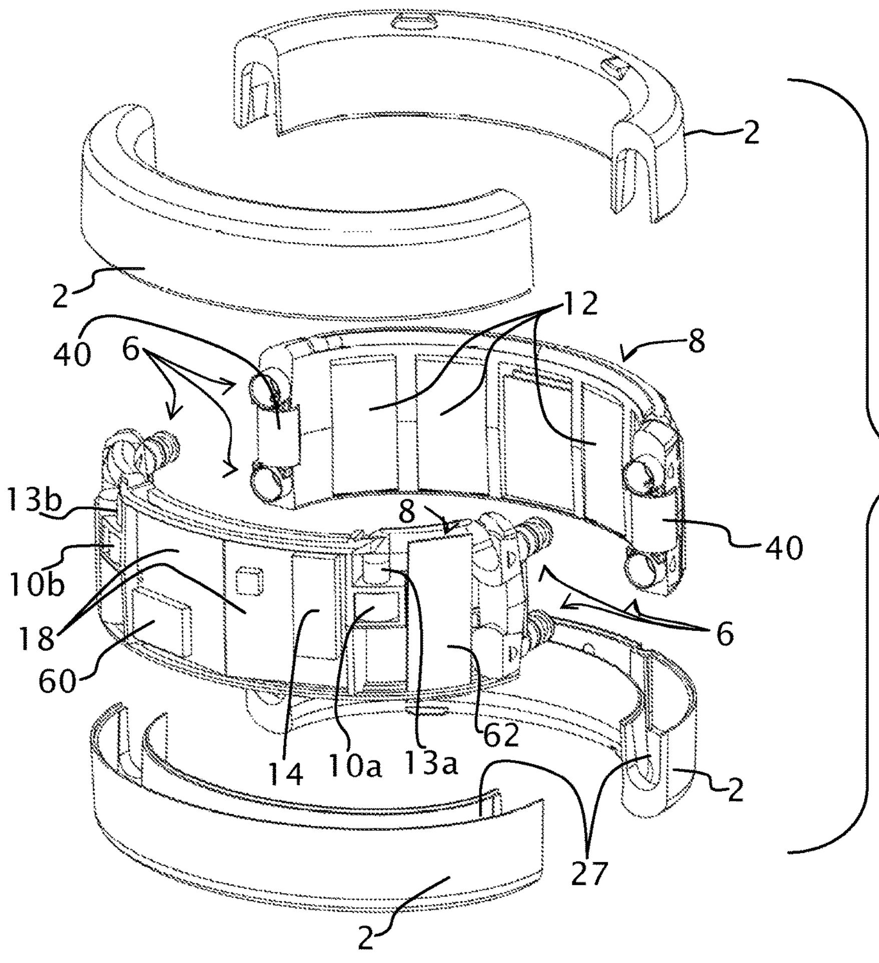
FIG 6c

FIG 8a
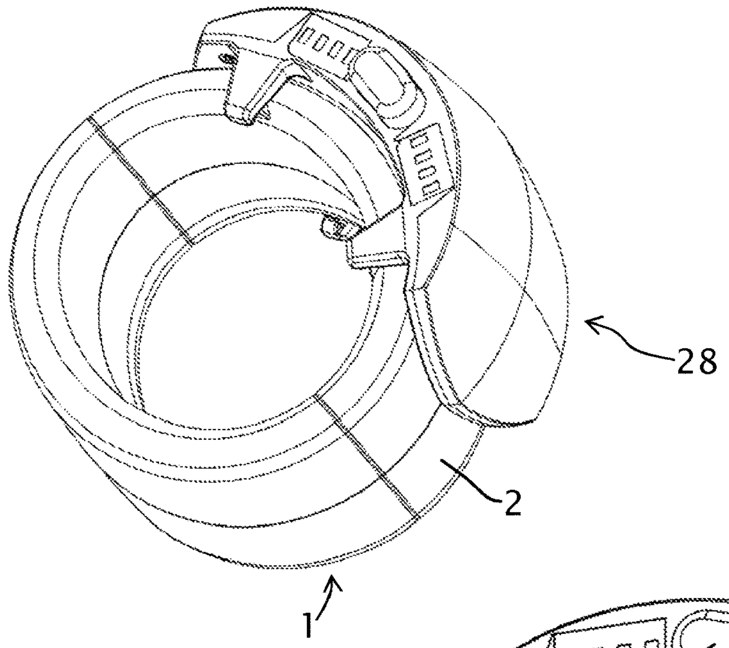
FIG 8b
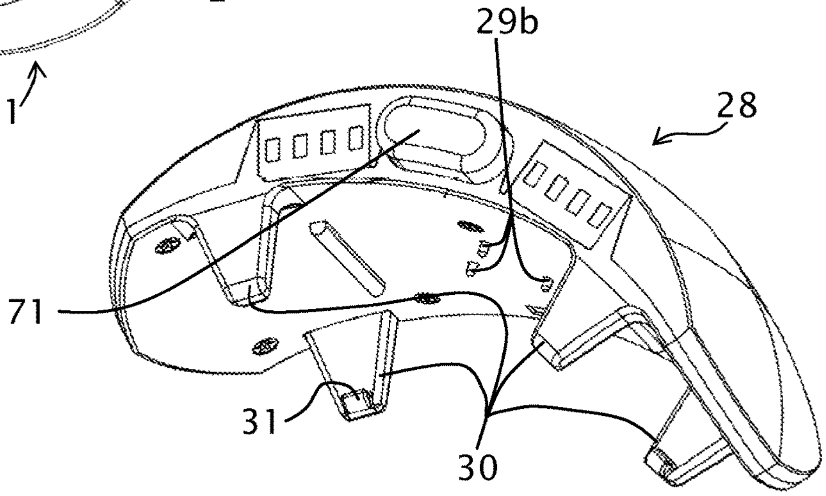
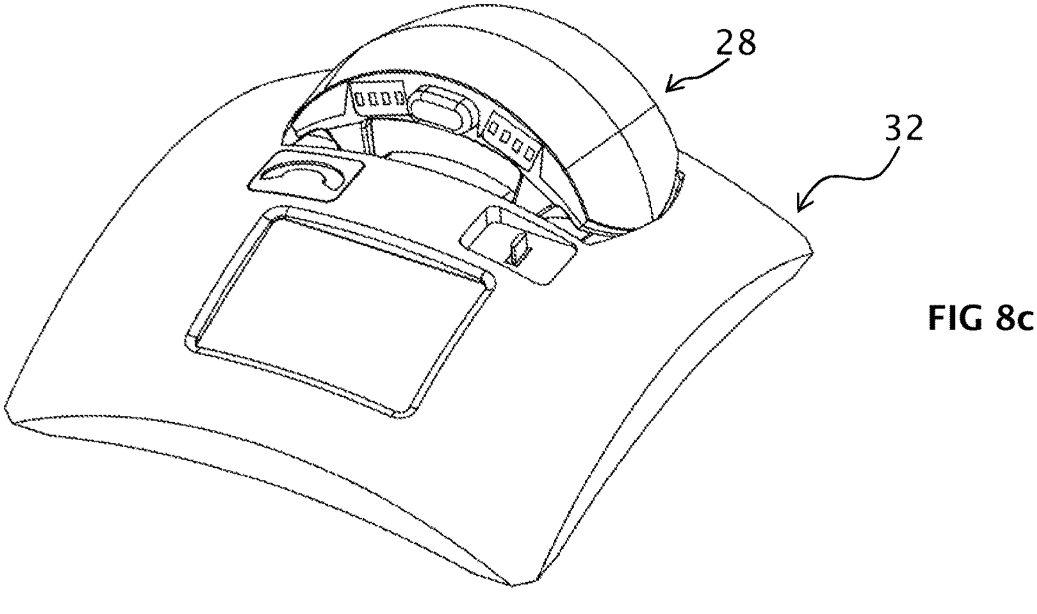
FIG 8c

ELECTRONIC MONITORING BRACELET

CROSS-REFERENCE TO RELATED APPLICATIONS

The present application is a national stage entry of International (PCT) Patent Application Number PCT/IB2012/057490, filed Dec. 19, 2012, which in turn claims priority to European Patent Application No. 11194712.3, filed Dec. 20, 2011, and European Patent Application No. 11194714.9, filed Dec. 20, 2011, the subject matter of which are expressly incorporated herein by reference.

The present invention relates to an electronic monitoring bracelet notably for monitoring the displacements of a person, for example within the scope of judicial oversight.

Certain persons suspected of having committed an offence awaiting judgment, or having committed an offence and being on parole, may be forced to wear an electronic monitoring bracelet so that the monitoring authority may localize the person and monitor his/her displacements at any time. Such bracelets contain a satellite localization system (called “GNSS”, acronym for Global Navigation Satellite System) such as for example GPS (Global Positioning System), a telecommunications system for transmitting data to a monitoring/control central unit and a system for detecting integrity of the bracelet in order to be able to detect whether the bracelet has been taken off or is faulty.

Indeed, in order to be able to monitor the displacement of the wearer of the bracelet at any time, it is necessary to ensure that the wearer cannot take off the bracelet without this being detected. The absence of a signal allowing localization of the bracelet or of a signal confirming integrity of the bracelet gives the possibility of reporting to the authorities non-compliance or non-authorized behavior of the wearer of the bracelet. It should be emphasized that the goal is not a bracelet which cannot be taken off, on the contrary, in the event of force majeure, the bracelet should be able to be taken off by pulling it off or by cutting it.

In a conventional device, the monitoring bracelet is intended to be attached around a wrist or an ankle of the wearer and comprises electric wires entirely encircling the bracelet and forming a closed electric circuit. In order to be able to take off the bracelet, the wearer has to sever the wire or disconnect the wire at one end, the opening of the electric circuit may be detected by a sensor mounted in the bracelet.

Conventional systems are however not sufficiently reliable over the typical durations of the wearing of the bracelets, or do not have sufficient protection against removal of the bracelet without any detection by clever means, such as bridging of the electric wires, or further they may transmit false non-integrity signals. It is sought to remove any situation of false positive (indication of non-integrity, while the bracelet is complete) and of false negative (indication of a complete bracelet, while the wearer has been able to undo the bracelet). It is also advantageous to reduce the monitoring costs, taking into account not only the cost of the bracelet but also the cost of tracing the bracelet on the wearer and of its replacement.

An object of the invention is to provide an electronic monitoring bracelet with an untamperable integrity detection system and which allows reduction or suppression of positive false alarms.

It is advantageous to provide an electronic monitoring bracelet, economical to make and to install.

It is advantageous to provide an electronic monitoring bracelet which has great autonomy.

It is advantageous to provide an electronic monitoring bracelet which is robust and reliable over a long time of use.

Objects of the invention are achieved with an electronic monitoring bracelet, comprising a ring-shaped body configured so as to be mounted around a limb or an object, and an electronic monitoring system positioned in the body comprising an integrity detection system, the ring-shaped body being in the form of a rigid shell containing a chamber or several chamber sections in which components of the electronic monitoring system are positioned, the ring-shape body entirely encircling the bracelet. The electronic monitoring system may notably further comprise a source of energy, a localization system and a communications system for transmitting monitoring and integrity data.

In an advantageous embodiment, the integrity detection system comprises a sensor configured for detecting a violation of the integrity of the rigid shell of the ring-shaped body. The sensor comprises a pressure sensor configured for detecting a pressure variation in the chamber or in one or more chamber sections contained by the rigid shell.

In an advantageous embodiment, the ring-shaped body is formed with two separate portions, configured so as to be mounted around a limb and locked together.

In an embodiment, the closing system is configured for irreversible locking without its destruction, the closing system comprising a weld at the interface of the body portions of the bracelet. In one variant, the interface of at least one of the portions of the body comprises an electric heating wire connected to an internal source of energy of the bracelet positioned near a surface of the interface and configured for heating by the Joule effect for carrying out welding of the two portions at the interface. The heating element may be connected to electronics positioned in the bracelet allowing the triggering of the welding at the interface by a wireless remote control.

According to an advantageous aspect, components forming the integrity detection system, the energy source, the localization system and the communications system are positioned in several areas distributed around the bracelet in the body.

In the present invention, a monitoring kit is also described, comprising an electronic monitoring bracelet and a mobile recharging unit without any wires, comprising one or more rechargeable batteries, and configured so as to be mechanically and removably coupled with the monitoring bracelet so as to carry out recharging of the internal energy source and this without any wire, the kit further comprising a recharging station for recharging the batteries of the recharging unit.

Objects of the present invention are also achieved by providing an electronic monitoring bracelet comprising a ring-shaped body configured so as to be mounted around a limb or an object, and an electronic monitoring system positioned in the body, the electronic monitoring system comprising at least an integrity detection system and an internal source of energy. The integrity detection system comprising at least one enclosure and at least one channel positioned in the body, the channel and the enclosure entirely encircling the bracelet and further comprising at least one sensor configured for detecting violation of the integrity of the channel or of the enclosure. The electronic monitoring system may further comprise a localization system, and a communications system for transmitting monitoring and integrity data.

In an embodiment, said at least one sensor comprises a pressure sensor. Said at least one pressure sensor may be positioned in the enclosure and configured in order to measure a variation of pressure in the enclosure and/or in the channel.

In another embodiment, said at least one sensor comprises an ultrasound sensor. In an advantageous embodiment, there are at least two ultrasound transducers, comprising an ultrasound transmitter and an ultrasound detector.

In a variant, the ultrasound transmitter may be positioned facing one end of the channel and the ultrasound detector facing the other end of the channel.

In a variant, the integrity detection system comprises at least one ultrasound sensor positioned in the enclosure. Said at least one ultrasound sensor positioned in the enclosure may be configured for detecting violation of the integrity of the enclosure, or also violation of the integrity of the channel.

The channel may be in fluidic communication with the enclosure, according to the variant.

In advantageous variants, the channel and/or the enclosure contains a fluid, the fluid may be an under-pressurized or over-pressurized gas or liquid relatively to atmospheric pressure.

In a variant, the monitoring system comprises an electronic card on which are mounted the communication system, the localization system and a source of energy, the electronic card being positioned in the enclosure, said at least one integrity sensor being mounted on the electronic card.

The communications system may advantageously comprise a transmitter configured for transmitting data over a mobile telephone network.

The localization system may advantageously comprise a sensor of satellite positioning signals (GPS). Depending on the field of use of the bracelet, in a variant, the localization system may additionally or alternatively comprise a wireless transmitter and/or receiver configured for communicating with a wireless receiver and/or transmitter of a base station in order to detect the presence of the bracelet in a communications area defined around the base station. The base station and the monitoring bracelet may for example each comprise a transceiver operating with one or more wireless communications protocols such as Bluetooth, WiFi, Zigbee or further other communications protocols. When the bracelet is no longer found in the wireless communications area, an alarm may be transmitted by the base station to a monitoring central unit.

In a variant, the body of the bracelet comprises a closing system allowing the setting into place of the bracelet around a limb or an object and comprises an attachment means which is irreversible except by definitively violating the integrity of the bracelet (voluntarily broken bracelets).

The attachment means may advantageously comprise welding of both interface portions of the bracelet.

Depending on the variant, the body may contain an orifice for producing a partial vacuum or an overpressure in the channel and/or the enclosure after setting the bracelet into place around a limb or an object, the orifice being sealed after being put under partial vacuum or overpressure.

Figure 1B:
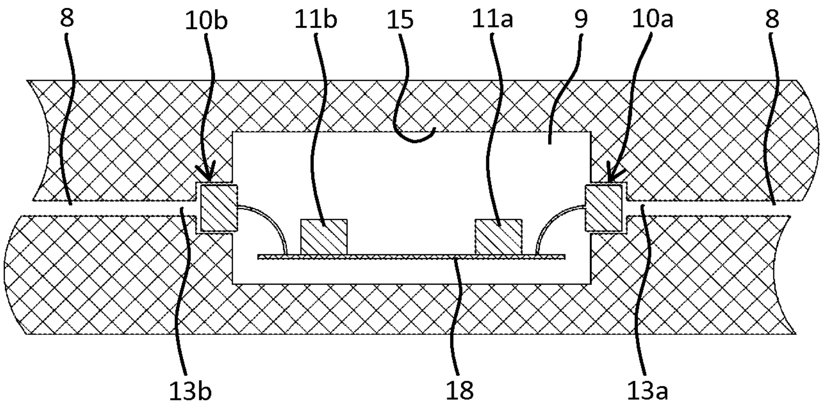

Other advantages, objects and aspects of the invention will become apparent upon reading the claims, as well as from the detailed description of embodiments hereafter and from the appended drawings, wherein:

FIG. 1*a* is a schematic sectional view of a monitoring bracelet according to a first embodiment of the invention;

FIG. 1*b* is a schematic sectional view of a portion of the bracelet of FIG. 1*a;*

Figure 2A:
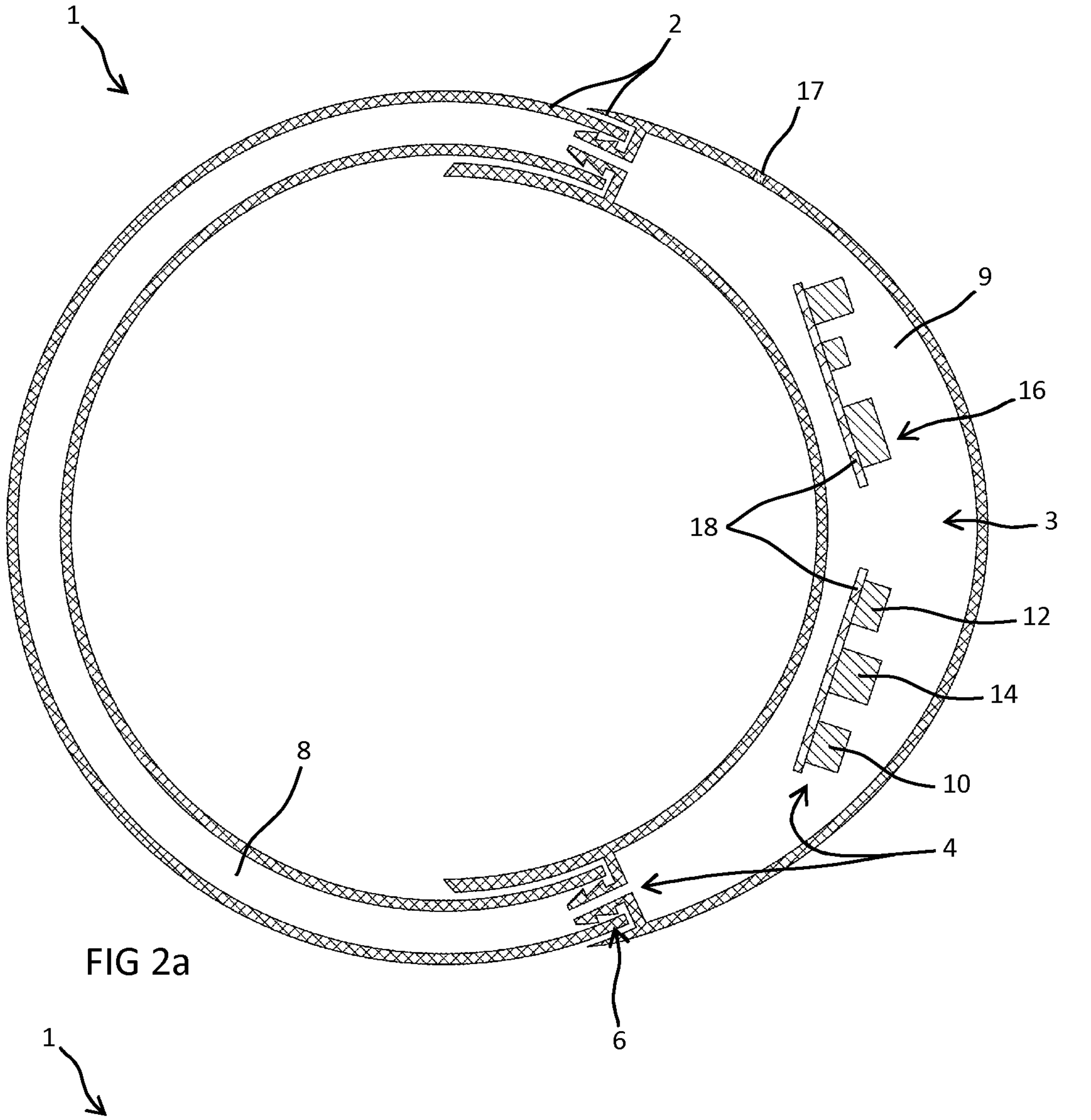
Figure 2B:
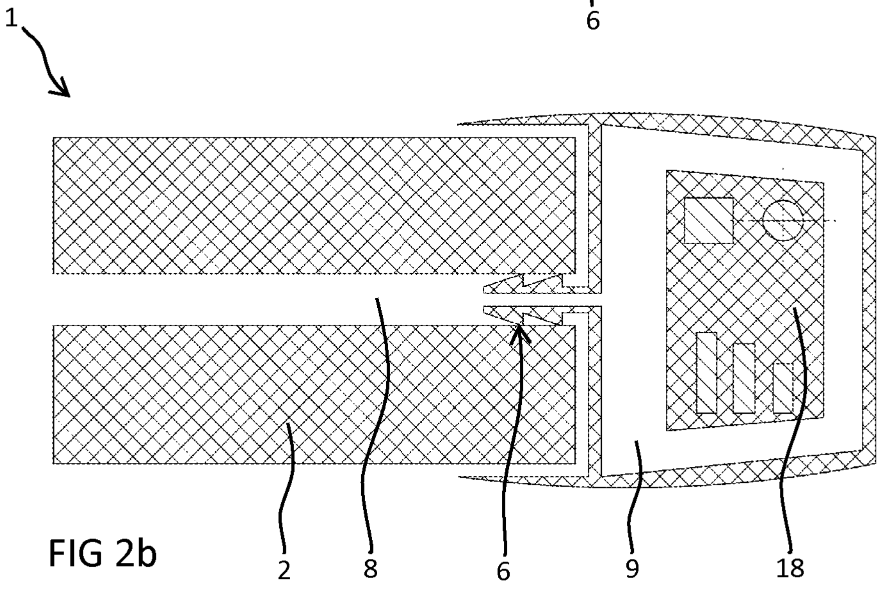

FIG. 2*a* is a schematic sectional view of a monitoring bracelet according to a second embodiment of the invention; and FIG. 2*b* is a schematic sectional view of FIG. 2*a*.

Figure 3A:
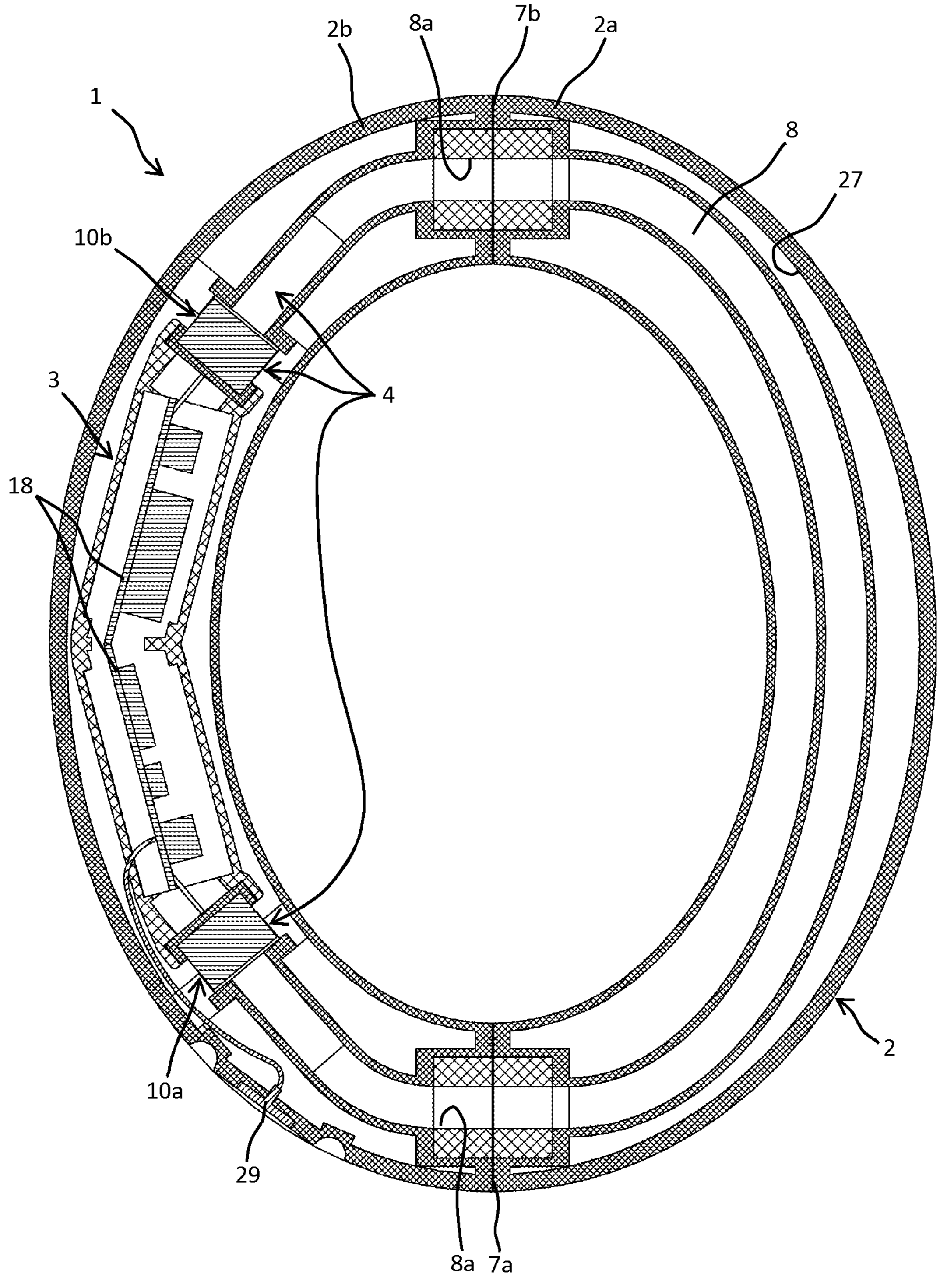
Figure 3B:
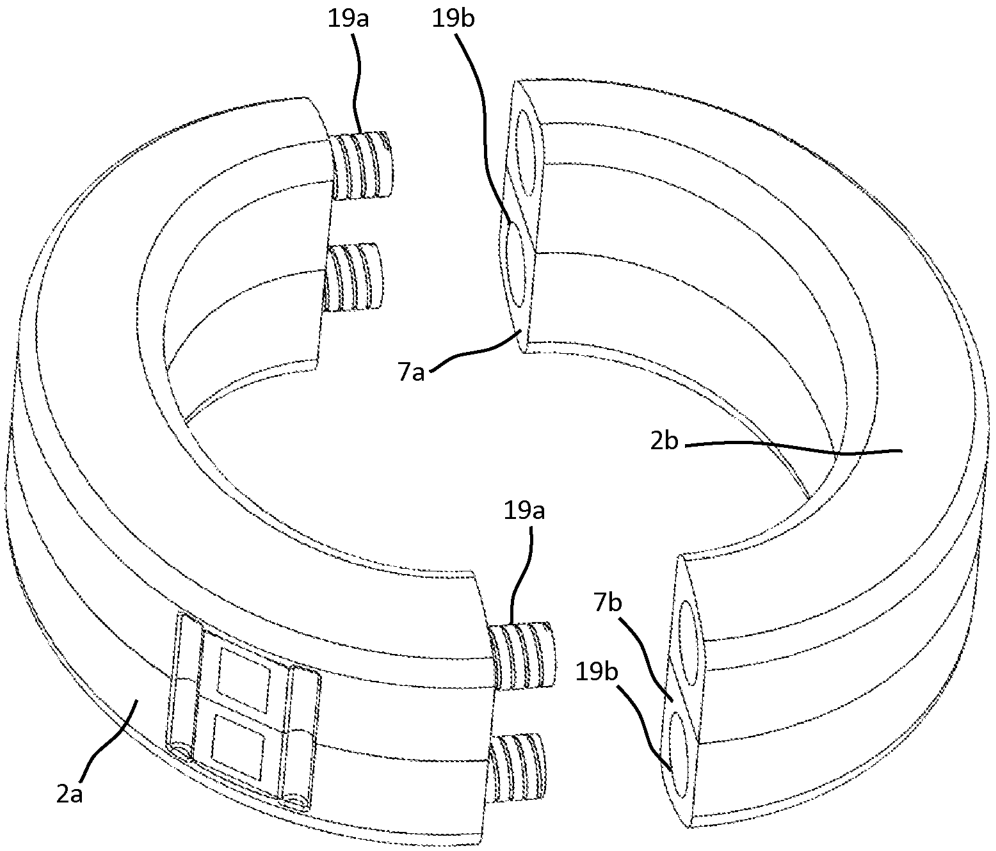

FIG. 3*a* is a schematic sectional view of a monitoring bracelet according to a third embodiment of the invention;

FIG. 3*b* is a perspective view of the monitoring bracelet of FIG. 3*a*, in two parts before its mounting.

Figure 3C:
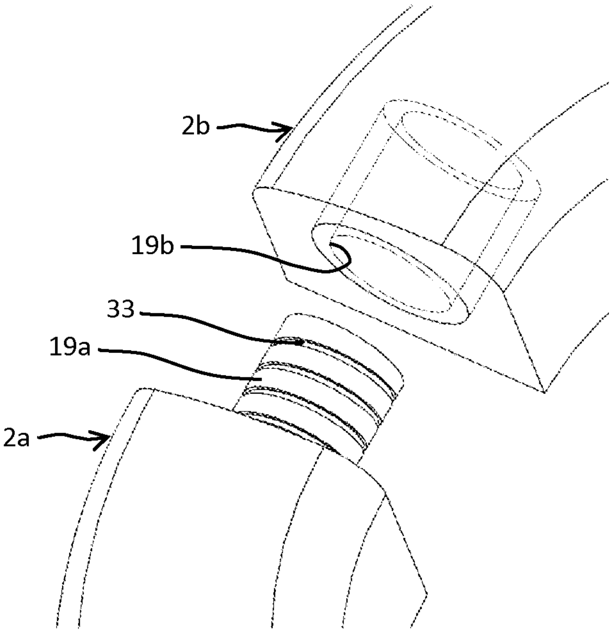

FIG. 3*c* is a detailed perspective view of a section of the closing system of the bracelet of FIG. 3*b;*

Figure 4A:
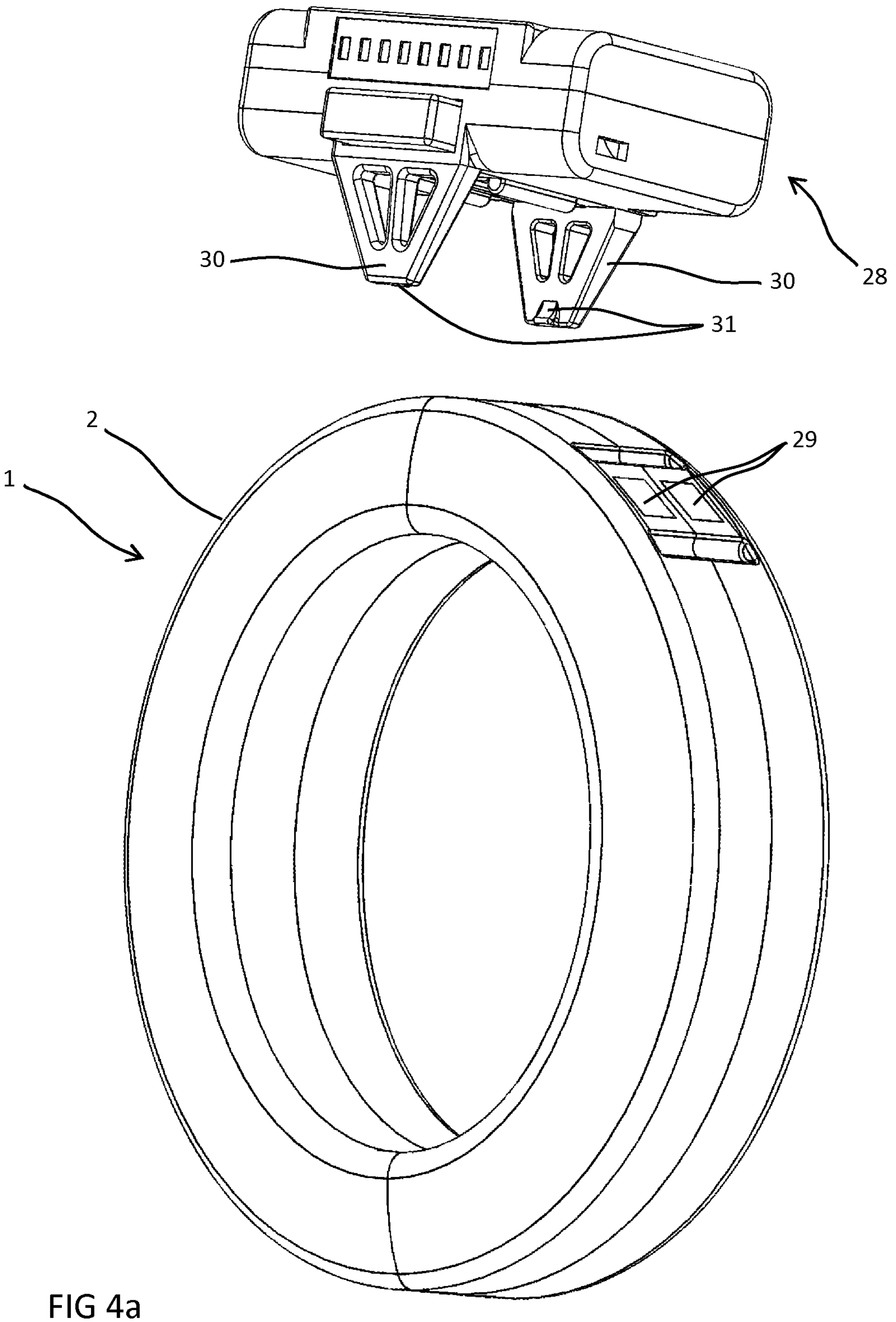
Figure 4B:
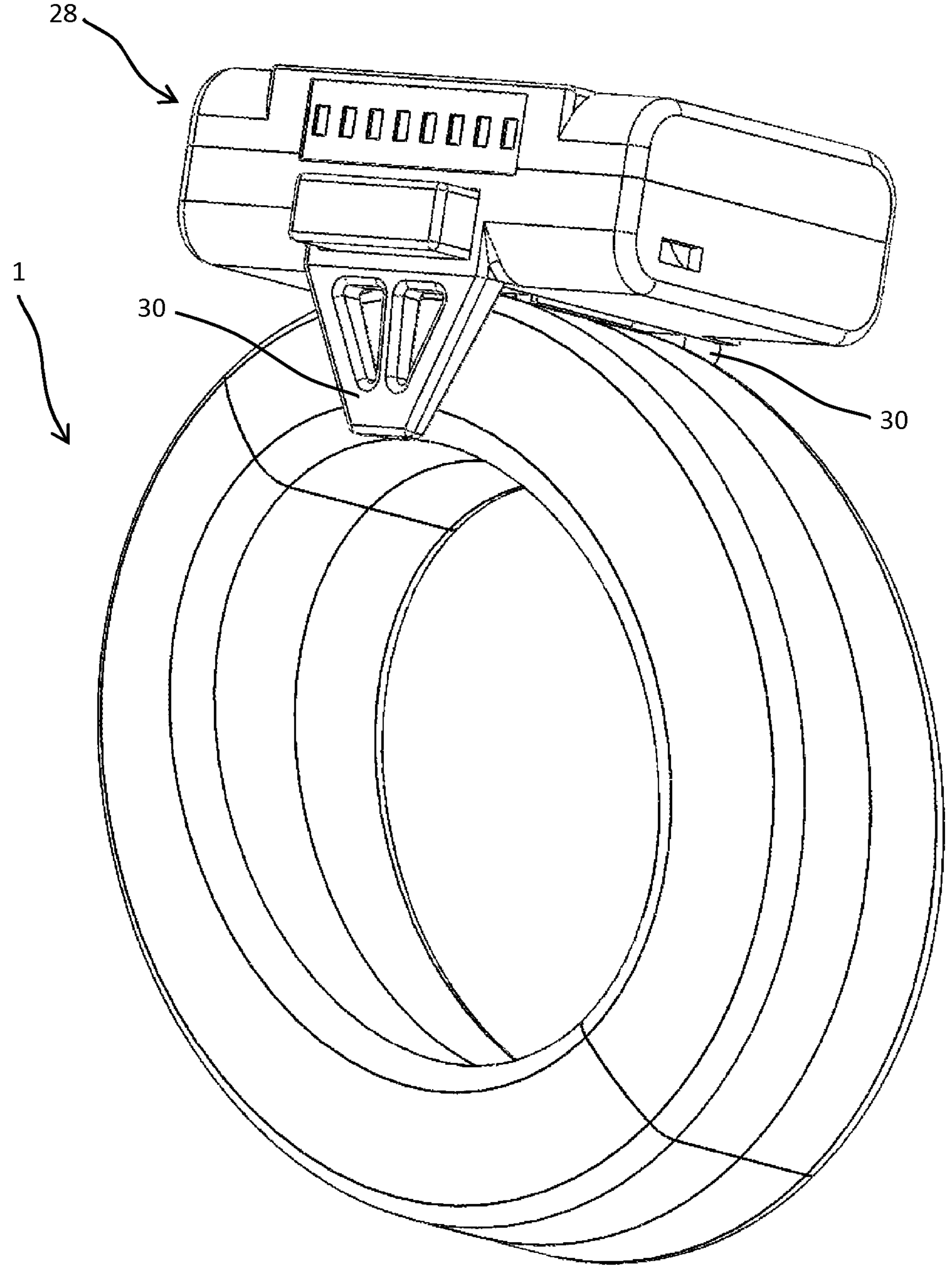
Figure 4C:
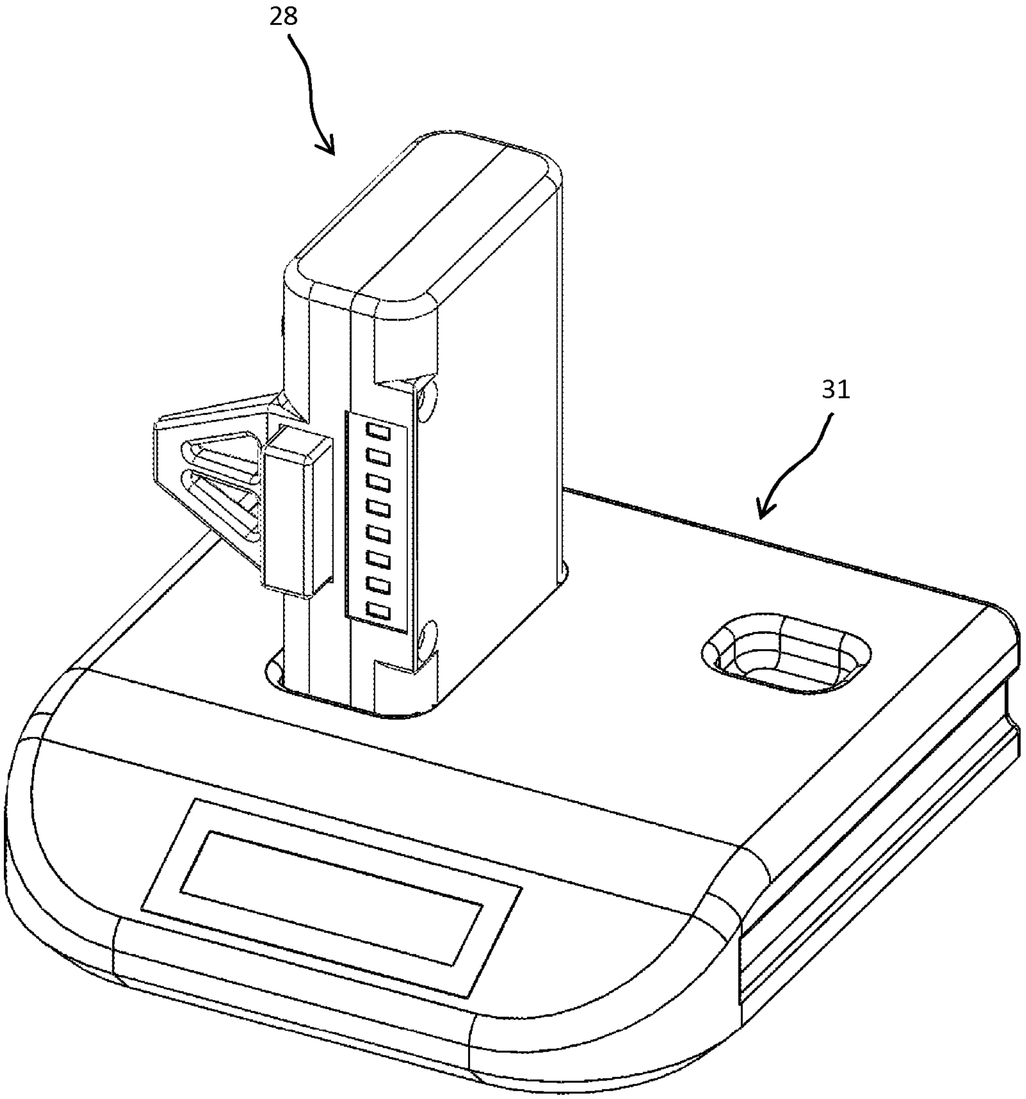
Figure 5:
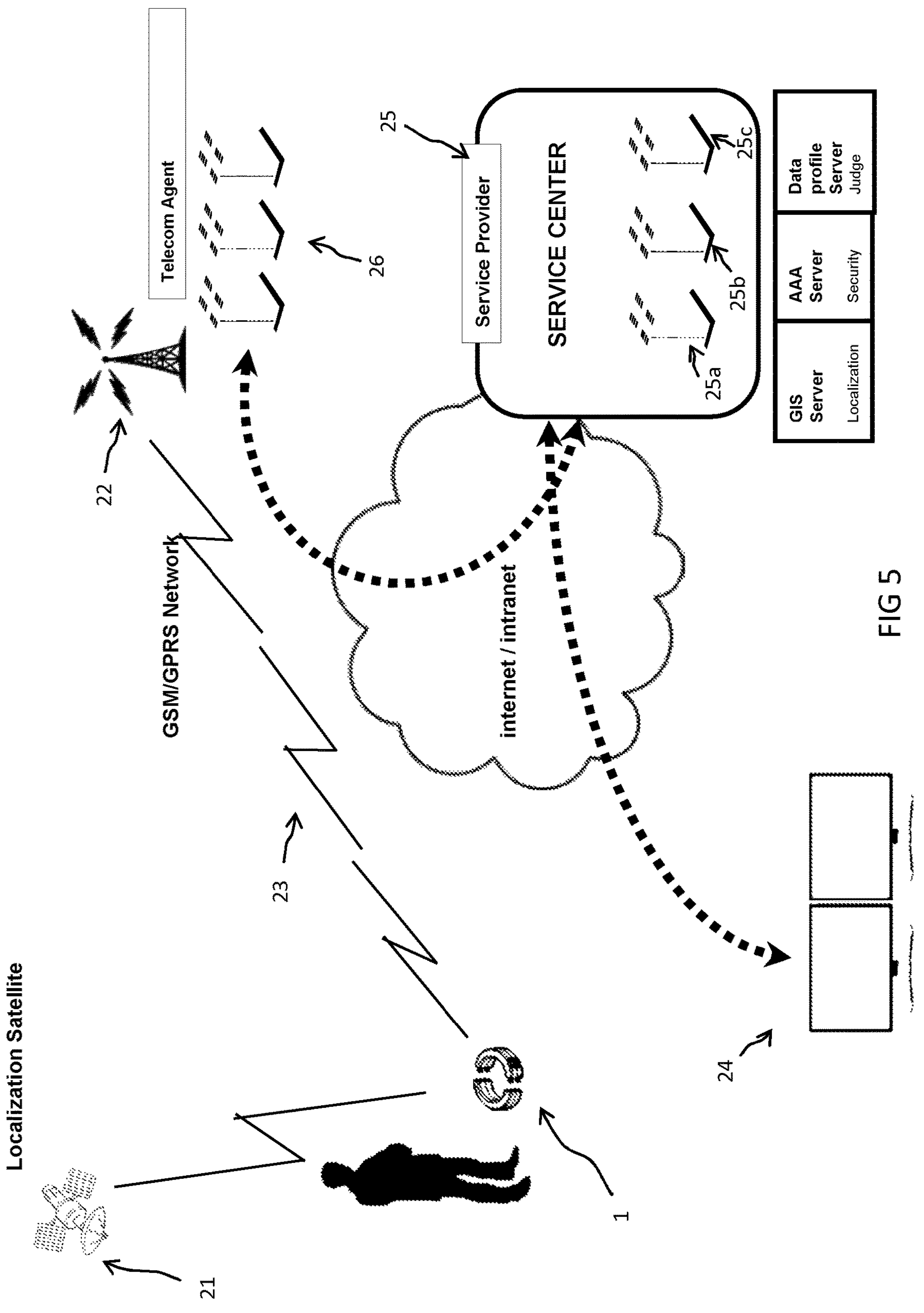
Figure 6D:
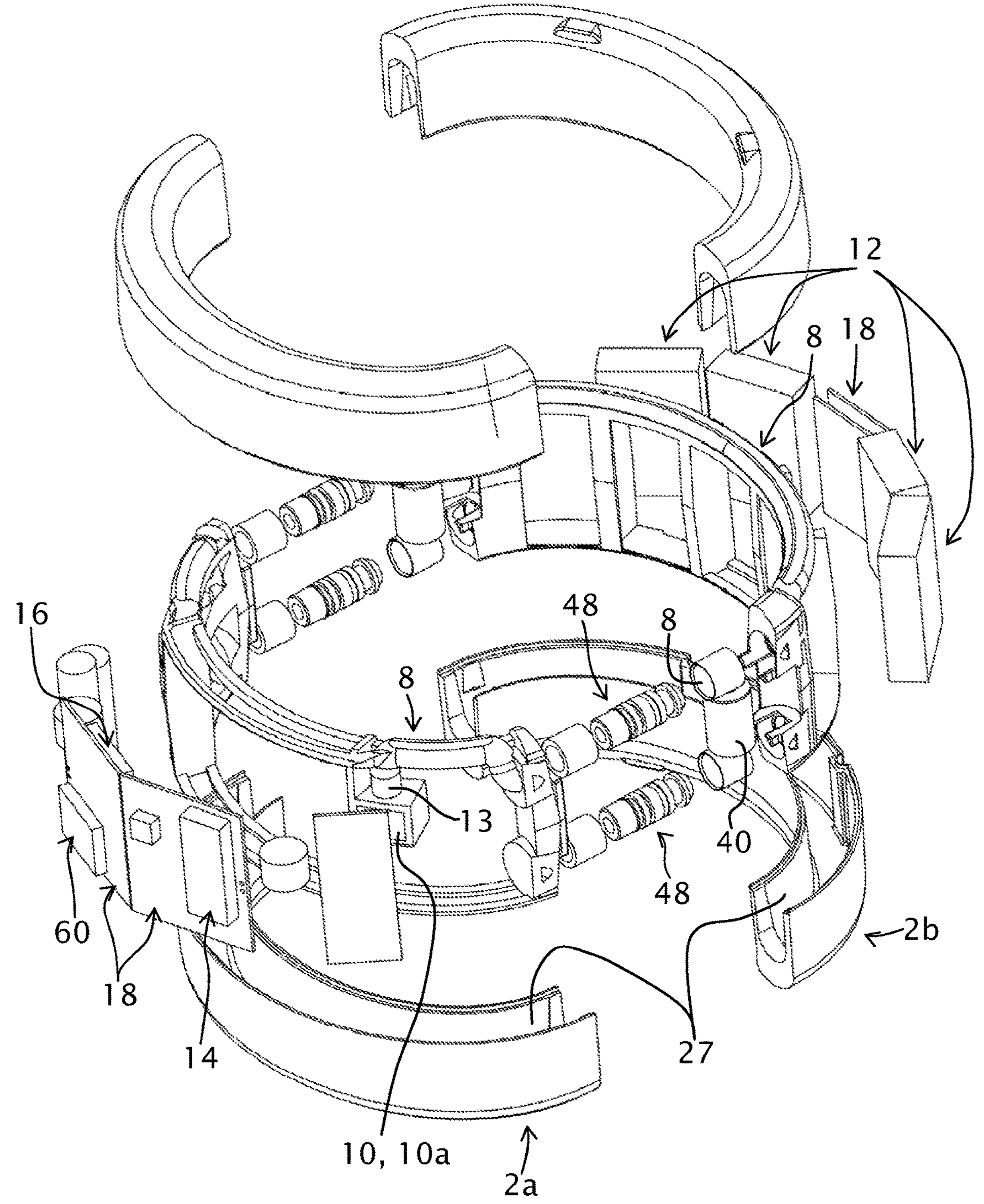
Figure 7:
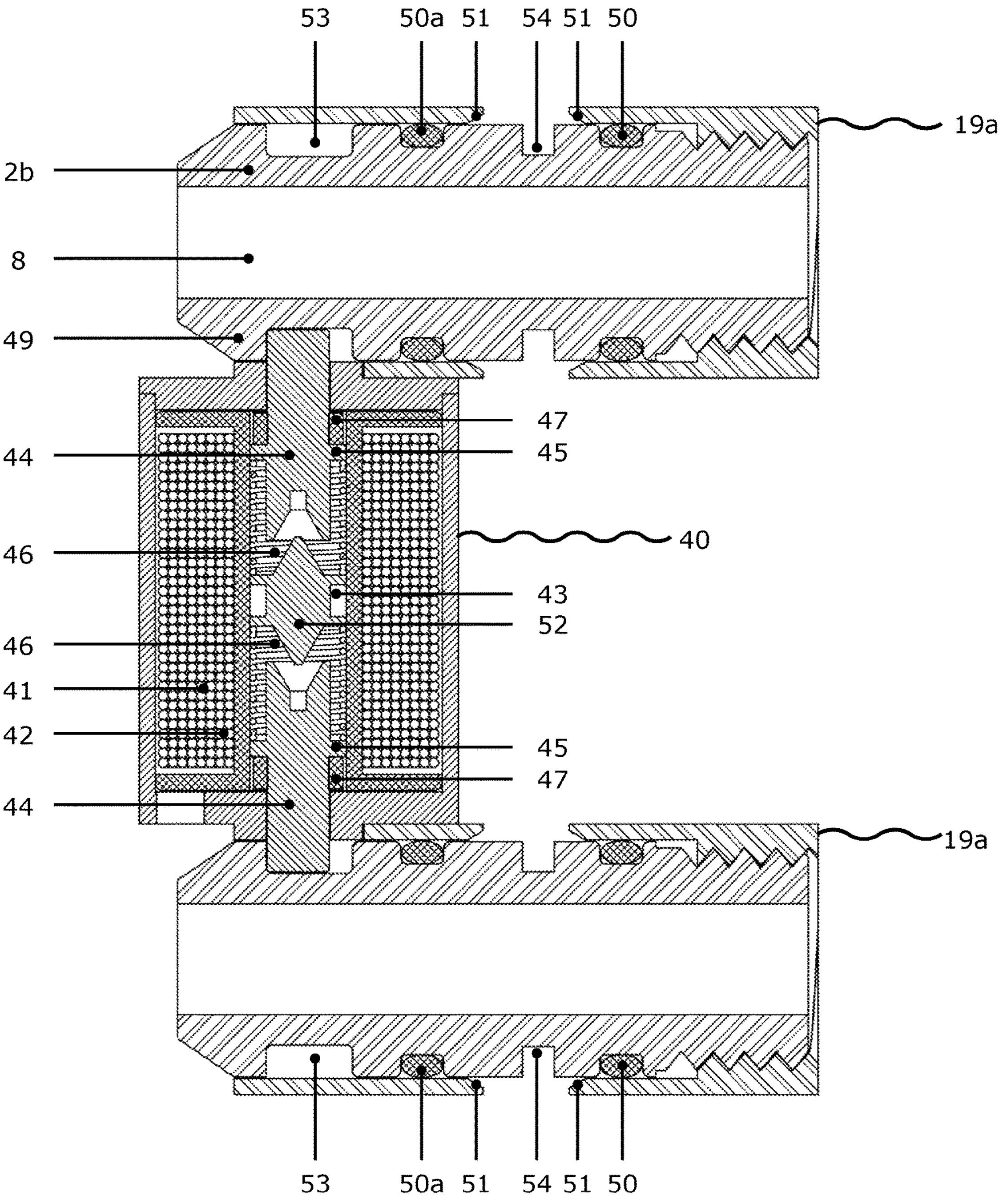

FIG. 4*a* is a perspective view of a monitoring bracelet and of an external source of energy for recharging the bracelet according to an embodiment of the invention;

FIG. 4*b* is a view similar to FIG. 4*a*, showing the external source of energy connected to the bracelet;

FIG. 4*c* is a perspective view of the external source of energy connected to a base station for recharging the external source of energy;

FIG. 5 is a diagram showing a monitoring bracelet within a global context of communications with external satellite localization systems, with data transfer via a mobile telephone system and processing of data on servers;

FIG. 6*a* is a perspective view of a monitoring bracelet according to an embodiment of the invention;

FIG. 6*b* is a perspective view of the monitoring bracelet of FIG. 6*a* in two parts before assembly;

FIG. 6*c* is an perspective view of the monitoring bracelet of FIG. 6*b* showing the rigid casing in exploded view;

FIG. 6*d* is an perspective view of the monitoring bracelet of FIG. 6*d* in exploded view;

FIG. 7 is a cross-sectional view of the reversible closing system of a monitoring bracelet according to an embodiment of the invention;

FIG. 8*a* is a perspective view of the monitoring bracelet of FIG. 6*a* and an external energy source for charging the bracelet according to an embodiment of the invention;

FIG. 8*b* is a view similar to FIG. 8*a*, showing the external energy source connected to the bracelet;

FIG. 8*c* is a perspective view of the external energy source connected to a base station for recharging the external energy source.

With reference to the figures, an electronic monitoring bracelet 1 according to different embodiments comprises a body or casing 2 with a general ring shape, configured so as to be mounted around a wrist or an ankle of a person, wearer of the electronic bracelet, and an electronic monitoring system 3 positioned in the body or the casing.

The electronic monitoring bracelet may also be used for applications other than that of the monitoring of persons, for example it may be placed around a system for closing a piece of property or any other valuable object for which monitoring is desired, notably for making sure that the object has not been opened, and further optionally in order to have a trace of the displacement of the object or of the piece of property.

Before use, the body of the bracelet is opened at least at one interface 7, but it may also be provided in two separate portions 2*a*, 2*b* forming two interfaces 7*a*, 7*b*, closed by a closing system 6.

The closing system may be an irreversible or permanent system, i.e. it cannot be reopened for taking off the monitoring bracelet without any damage to the bracelet, representing violation of the integrity of the bracelet. The closing system may comprise mechanical means, such as a connector formed with protrusions (for example an arrow head) or tabs on one portion inserted into an orifice or mating cavity (for example with shoulders for engaging the protrusions or tabs) on the other portion. After insertion, the separation of the portions of the connector is blocked. The closing system may also comprise a weld, for example an ultrasonic weld, or an adhesive bond by an adhesive at the interface of the bracelet portions coupled together. The closing system may also comprise a combination of a mechanical attachment of both portions of the bracelet in the closed position and of an adhesive bond or weld of the coupling interface. The closing system may also comprise crimping, for example a metal ring crimped around the coupling interface.

In an alternative embodiment, the closing system may be a reversible system with a locking system which may be opened with a key or an electronic code so as to be able to take off the bracelet without any destruction.

With reference to FIGS. 3*a* to 3*c* and FIGS. 6*b* to 6*d* and 7, the closing system 6 comprises an extension or projection 19*a* projecting from the interface 7 of one of the body portions 2*b*, configured so as to be inserted and accommodated in a mating cavity 19*b* on the other portion of the body 2*b*. There may only be one pair of mating projection and cavity, or several mating projection and cavity pairs. In the case of a plurality, the projections may be all located on the same portion of the body, or distributed over both body portions. The mating protrusions and cavities are preferably configured so as to allow only one way for assembling both body portions 2*a*, 2*b* according to a single orientation, in order to avoid that body portions may be put together in a wrong direction. The extension 19*a* may be in the form of a tube with a channel portion 8*a* aligned with and forming a portion of the channel 8 surrounding the monitoring bracelet. The tube portion may be integral with or pre-assembled in one of the portions of the body 2*a*, for instance a tube portion 48 threaded to the body portion 2*a* as illustrated in FIG. 7, or be in the form of a separate part inserted into cavities in both body portions 2*a*, 2*b* when the monitoring bracelet is closed. Seals 50*a* (see FIG. 7), for instance in the form of O-rings, may be arranged around each extension 19*a* and between the extension 19*a* and the complementary cavity 19*b* to hermetically close the canal 8 at the interface between the two body portions 2*a*, 2*b*. The seals 50 may also be arranged around the threaded tube portion 48 at the body portion 2*a* to ensure a hermetic connection between the two portions.

In a variant, as illustrated in FIGS. 3*a* to 3*c*, the extension and/or the mating cavity comprises, close to its surface or at its surface, an electric heating wire 33 connected to a source of electric energy positioned in the body of the bracelet and configured for providing heat energy melting the plastic type material at the surface of the extension and/or of the cavity for welding both portions at their interfaces. The wire therefore produces heat energy by the Joule effect. Triggering of the heating may be controlled by the electronic circuit of the monitoring bracelet and be remote-controlled, for example from a monitoring central unit 24 via the mobile telephone system, or controlled from nearby through a wireless connection. The closing of the bracelet may thus be controlled by a monitoring central unit, or may be controlled and carried out by an operator on site during the setting into place of the monitoring bracelet.

In a variant, a very fine conducting wire is wound around the extension in a small groove, for example a helicoidal groove at the surface of the extension 19*a*. Alternatively, the wire is positioned close to the outer surface of the extension, but overmolded and consequently under the outer surface. The welding of an extension tube in a mating cavity gives the possibility of ensuring hermetic closure between both portions of the body and notably of the channel 8 in the bracelet. An electric heating wire may also be provided at the surface of the interface of the body positioned around 7*a*, 7*b* for also welding the faces which will abut against each other, of both body portions.

In a variant, instead of a weld between the portions of the body 2*a*, 2*b*, it is also possible to provide a closure by means of an adhesive or on another thermally or optically activatable binder by means of a light-emitting diode positioned in the interface.

Referring to the embodiment illustrated in FIGS. 6*b* to 7, the closing system 6 is a reversible system with a locking mechanism that can be opened with an electronic key or code such that the bracelet can be removed without destruction. The closing system comprises an electromagnet 40 mounted in a body portion 2*b*, comprising a coil 42 and one or two plungers 44 slidably mounted in a cavity 43 at the centre of the electromagnet, each biased by a compression spring 46 in a closed position where they are inserted in a complementary cavity 53 in the extension 19*a* of the other body portion 2*a*. The compression springs can press on a core 52 situated in the centre of the coil. The travel of each plunger is limited towards the exterior by a shoulder 45 formed on the plunger engaging a stop in the housing 41 of the closing system. In the illustrated example, the stop comprises a rest 47 in a non-magnetic material, for instance plastic, that also allows the magnetic field to circulate in the body to avoid a dead-zone in the retraction.

On closing, the tapered form 49 of the extremities of the extensions 19*a* facilitate the penetration and push the plungers 44 in the electromagnet. An angle 51 provided at the entry of each cavity 19 allows guiding and compression of the seal 50*a*. In the fully closed position, the two bracelet halves are interlocked, the extensions 19*a* penetrating in the cavities 19*b*, and the plungers 44 are pushed in a closed position where they are inserted in the complementary cavities 53.

On opening, the electronic control mounted in the bracelet supplies power to the electromagnets of the locks placed on each side of the bracelet. The excitation of the electromagnets attracts the two plungers 44 that thereby disengage the cavities 53.

Since it is desirable to guarantee the closing of the four attachment points of the bracelet, two current sensors are placed on the supply line of each of the two electromagnets. The position of the two plungers notably modifies the self-inductance measured at the terminals of the solenoid (coil), which enables precise determination of whether the two plungers are well inserted in the cavity 53 of the two sleeves or not. This measure can be achieved by imposing a voltage pulse on the solenoid while measuring the time to generation of a current flowing therethrough. The actuator is designed such that the self-inductance varies significantly according to the position of the plungers, on the one hand in order to facilitate the measurement, but also to reduce the excitation current as soon as the plungers are retracted in order to save energy. Moreover, as the residual magnetic field may over time prevent one or both of the plungers to retract, the control device enables inversion of the excitation current in order to suppress the residual field and thus guarantee that the two plungers retract after the opening cycle.

For reasons of personal safety, when exceptional conditions render it indispensable, it may be necessary to cut through the bracelet (car accident, stuck limb, etc). The function of the invention is to ensure that a separation is always detected, but not to prevent such separation. The possibility of cutting through the bracelet may be facilitated by a groove 54 forming a mechanical fuse on the sleeve in such a manner that the thickness of the remaining material in the section of the groove may be broken, for instance by first aid personnel, or forcefully torn off.

Referring especially to FIGS. 3*a*, 5 and 6*d*, the monitoring system integrated into the body comprises an integrity detection system 4, a source of energy 12 such as a lithium battery for powering the electronic circuit, a localization system 14 and a communications system 16 for transmitting monitoring data to a monitoring central unit 24 and optionally a short range wireless communications system 60 functioning with one or more communication protocols such as the protocols known under the names Bluetooth, Wi-Fi, or Zigbee. With reference to FIG. 5, the localization system may notably comprise a satellite positioning system (a so-called "GNSS", acronym of "Global Navigation Satellite System") such as for example GPS (Global Position System), the localization system comprising an antenna for receiving the signals transmitted by a satellite 21 and a processing circuit for calculating the terrestrial position of the bracelet, this system being known per se. Other localization systems may be used as a replacement for the GPS system, or in parallel, notably for localizing the bracelet inside a building or a structure not allowing access to the signals of satellites 21. Depending on the field of use of the bracelet, the localization system may comprise a wireless transmitter and/or receiver configured for communicating with a wireless receiver and/or transmitter of a base station in order to detect the presence of the bracelet in a communications area defined around the base station. The base station and the monitoring bracelet may for example each comprise a transceiver, or one a transmitter and the other one a receiver, operating with one or more wireless communications protocols such as the protocols designated as Bluetooth, Wi-Fi, Zigbee or further other wireless communications protocols. When the bracelet is no longer in the wireless communications area, an alarm may be transmitted by the base station to a monitoring central unit. The localization system may also be based on or comprise a positioning system relatively to a mobile telephone system or other public or private wireless networks.

The communications system 16 for transmitting monitoring data is preferably based on a communications system through the mobile telephone network 22 using communications protocols known for transmitting data, such as GPRS, EDGE or other ones according to the communications systems used on the monitored territory. The transmitted data 23 may notably comprise an identifier of the bracelet or else an authentication code, the position of the bracelet provided by the localization system 14 and a piece of information reporting the condition of the bracelet, i.e. either a normal operating condition, or an abnormality which triggers an alarm requiring the intervention of the monitoring authority. The communication system may also transmit other information, such as the charge condition of the battery or further a history over a given time on the localization of the bracelet stored in memory in the bracelet. The monitoring data are preferably encrypted before their transmission, in order to avoid tampering or unauthorized reading of the data.

The data 23 transmitted over the mobile telephone network 22 may, in a first phase, be received on the server 26 of the mobile telephone network operator, and then be transmitted to servers 25 for example through the so-called "internet" network route by means of a secured communication, the data being stored on the server 25 and accessible by means of a connection secured and authenticated by the monitoring central unit 24. In order to ensure the confidentiality of the monitoring data, these data may be distributed over several servers 25*a*, 25*b*, 25*c*, the reconstruction of the data requiring special codes and software packages.

The source of energy, the localization system, the communications system as well as the electronic part of the integrity detection system 4 may be mounted on one or more electronic cards 18 positioned in an enclosure 9 for the electronics in the body or casing. It is also possible to have electronic components distributed in two or three locations in the casing of several electronic cards with a rigid or flexible substrate. However, in a preferential embodiment, the electronics is concentrated on a single card in order to reduce the manufacturing costs. The enclosure 9 may be filled with a gas or contain a gas, or may be filled with resin poured around the electronics in order to protect the components.

In an advantageous embodiment, different elements installed inside the body or casing 2 may be distributed in the body in different locations, entirely encircling the body in order to distribute the weight, and also allow reduction in the section of the body for better comfort of use and also more discreet wearing of the monitoring bracelet. Indeed, in conventional monitoring bracelets, the whole of the active components are typically gathered in a casing coupled with a flexible bracelet, only the bracelet surrounding the ankle or the wrist entirely. In this conventional bracelet, the casing is therefore positioned only on one side of the ankle or of the wrist. In the invention, the distribution of the components inside the bracelet also allows an increase in security against an attempt to deceive the integrity maintenance system, the position of the various components inside the casing not being known specifically. In order to distribute the components in the casing, it is for example possible to have the electronic card on one side of the bracelet and the source of energy, notably a battery, on the other side of the bracelet.

In advantageous embodiments, the integrity detection system comprises a channel 8 (which will be called also a "ring-shaped channel") hereafter extending from one end of the enclosure 9 for the electronics to the other end of the enclosure thereby entirely encircling the bracelet. The integrity of this channel 8 and of the enclosure 9 allows definition of the integrity of the electronic monitoring bracelet being used, by means of at least one sensor 10, 10*a*, 10*b*, 11*a*, 11*b* which may be, in a preferred embodiment, positioned or mounted at least partly in the enclosure 9.

In a preferred embodiment, the channel contains gas. In other variants, the channel may contain a solid or another material conducting ultrasound with a different impedance to acoustic waves, of the body or casing surrounding the channel.

In the embodiments illustrated in FIGS. 1 and 6*b* to 7, the sensor 10 comprises a generator or transmitter of ultrasound 10*a* and a detector of ultrasound 10*b*, the transmitter being positioned at one end 13*a* of the channel 8 configured for generating acoustic waves, notably in the range of ultrasound frequencies (30 kHz to 100 kHz), in a channel so that the waves progress along the channel as far as the ultrasound detector 10*b* positioned at the other end 13*b* of the channel. The acoustic signal sensed by the detector is a function not only of the acoustic signal generated by the ultrasound emitter, but also on the geometry of the channel, notably the length or shape of the channel as well as on the properties of the fluid (or depending on the variant, of the solid) filling the channel. An extension of the channel, even by a fraction of a millimeter may be detected. The crushing or change in shape of the channel may also be detected. The ultrasound generator may be configured in order to generate an ultrasonic signal with specific shape and duration, parameterized beforehand, this acoustic signal may be unique, i.e. different from one bracelet to another, or the same depending on the intended security level.

A significant advantage of the use of an ultrasound generator and detector for verifying the integrity of the channel entirely around the bracelet is the low consumption of energy and therefore the greatest autonomy, while ensuring very reliable detection as well as a very robust system. The acoustic signal may be transmitted with very short pulses, with a duration of a few microseconds, at intervals shorter than 1 second, or even at greater intervals if larger autonomy is desired.

In order to check the integrity of the enclosure 9 for the electronics, in a variant, there is also an ultrasound transmitter 11*a* and an ultrasound detector 11*b* positioned in the enclosure in separate positions, for example mounted on the electronic card 18 and directed towards a wall 15 of the enclosure, operating according to the same principle as the sensors 10*a*, 10*b*. Breakage or crushing of the enclosure 9 has an influence on the acoustic signal and may be detected.

In a variant, it is possible to have a single pair of sensors comprising a detector and a transmitter, positioned in the enclosure 9 and configured for transmitting the ultrasound signal so that it does not only cover the channel 8 but also the enclosure 9, allowing a reduction in the number of components.

In variants, it may also be contemplated to have a single ultrasound sensor having a transmitter and detector function, positioned at one end of the channel 8 and/or in the enclosure 9 and configured so as to transmit an ultrasound signal and then to detect it a few microseconds later when the signal will have covered the full perimeter of the bracelet and/or will have been reflected from the wall of the enclosure.

The ultrasound module generates on the one hand an ultrasound signal and on the other hand captures and analyses the signal generated. The ultrasound signal may have for instance a frequency of 40 kHz, but other ultrasound frequencies may also be suitable, and may be steady or pulsed. In steady mode, the phase is measured whereas in pulse mode the travel time may be measured. Both cases may also be used to determine the pulse response of the channel.

In order to measure the phase, the ultrasound signal may be generated as a steady signal; once the signal is stable the phase is measured over a plurality of periods in order to obtain an instantaneous average. Once the measurement is terminated, the phase is calculated and the signal generation is stopped.

In order to measure the travel time, the ultrasound signal may be produced in pulsed manner and one waits for the signal to propagate through the channel. In chosen time, the acquisition of the signal is switched on and is effected over a number of tens of periods of the ultrasound signal. The amplitude of the received signal more or less follows a Gauss curve. Once all the measurements are recorded, the position of the maximum amplitude is calculated and the signal travel time is deduced.

The ultrasound transducer takes time to start the oscillations and when a short excitation is applied, the amplitude of the signal increases from period to period, and once the excitation is stopped, the transducer continues to oscillate with a decreasing amplitude. The generated signal, and thus the received signal, will thus be formed of a plurality of oscillations having an amplitude following a sort of Gauss curve.

In order to measure the pulse response, the signal may be generated in a steady or pulsed manner. The form of the pulse response of the channel depends on its geometry. The physical conditions influence principally only the general parameters of the pulse response and not the general form thereof provided that the physical conditions remain within the field of normal living conditions.

In the three preceding cases, the signal processing takes into account the physical conditions found in the bracelet, in particular the temperature and pressure of the air, as well as the composition of said air, which impacts its density and thus the propagation velocity of sound in the channel.

In order to optimize the measurement algorithm parameters, an auto-calibration is effected when the bracelet is put in place to take into account the possible variations in shape of the channel or of the gaseous composition of the air.

In an embodiment, the integrity detection system comprises a static pressure sensor 10 positioned in the enclosure, or further at one or both ends of the channel 8, configured for detecting a pressure variation in the channel and/or in the enclosure, either an increase in pressure or a decrease in pressure, or both. When the pressure variation is beyond a predetermined threshold, an abnormality is reported. In this embodiment, the enclosure and the channel are filled with a fluid at a pressure different from atmospheric pressure, i.e. a partial vacuum or an overpressure. When the integrity of the channel or of the enclosure is affected, notably if the channel or the enclosure is pierced, the pressure drop in the case of overpressure or the increase in pressure in the case of a partial vacuum is detected by the pressure sensor. The fluid may simply be air, notably in a variant with an enclosure and a channel in a partial vacuum. The fluid may also be a gas with large molecules, such as nitrogen, notably for overpressure variants, in order to reduce the diffusion rate of gas molecules through the body causing a drop of pressure over time. An orifice 17 through the body allows the air to be removed before sealing the orifice. It is also possible to use the orifice for injecting a gas in order to over-pressurize the enclosure in the channel.

According to an advantageous aspect of the invention, the casing 2 of the bracelet may be in the form of a rigid or semi-rigid shell forming a closed circuit, i.e. a self-bearing shell which provides some resistance against its crushing. This gives the possibility of protecting the components positioned in a chamber 27 formed inside the casing. The casing 2 is therefore in the form of a shell containing a chamber in which are positioned the various components. In conventional bracelets, the electronic portion is positioned in a box which is attached or mounted on a flexible belt, forming the bracelet which encircles the ankle of the wearer. The weight and the bulkiness of the electronic box positioned on an outer side of the ankle are uncomfortable and exposed to impacts causing failures or involuntary breaking of the monitoring bracelet. In the invention, the essentially smooth shell and with an essentially constant or homogeneous section entirely encircling the bracelet does not provide any shoulder or protrusion which may be caught by external objects and, in the case of a rigid or semi-rigid shell, provides protection against external impacts. An important advantage of this aspect of the invention is that the various electronic components, such as the electronic circuit board 18, the batteries 12, the mobile communication antenna 62 and other components may be distributed all around the bracelet in the interior 27 of the ring-shaped rigid casing 2 to distribute the weight and reduce the thickness and volume of the bracelet while increasing reliability, security and comfort.

It is also possible to have inside this casing 2, a partial vacuum or an over-pressurized gas relatively to ambient pressure, in order to detect violation of the integrity of the casing by detecting a variation of pressure with a pressure sensor positioned in the casing. The chamber 27 inside the shell-shaped casing 2 may therefore have the function of the channel 8 described earlier instead and in place of the channel 8 illustrated in the variants of FIGS. 2*a* to 3*b* and 6*a* to 6*d*. It is however possible, as illustrated in FIGS. 2*a*, 3*a*, 3*b*, and 6*a* to 6*d*, to combine a channel 8 formed with a dedicated tube, entirely encircling the bracelet, positioned in a rigid shell formed by the casing. In this case, it is possible to have different overpressure or partial vacuum levels in the channel 8 and in the chamber 27 of the casing 2 around the tube forming the channel, or further have a pressure different from the ambient temperature in the chamber 27 and ambient pressure in the channel in order to have several means for detecting violation to the integrity of the monitoring bracelet. For example, in the case of an overpressure or a partial vacuum in the chamber 27 of the casing 2, it would be possible to send a signal for violation of the integrity of the bracelet before the loss of energy and before the electronic circuit may be reached. It would thus be possible to transmit an integrity violation signal which would allow triggering of the alert and a more rapid intervention instead of waiting for the triggering of the alarm due to non-response of a monitoring bracelet which would be destroyed. Indeed, in the conventional system, if the electronics are destroyed or the power supply of the electronics is cut, so that it cannot transmit the failure signal, depending on the circumstances, this may take a few minutes before the alarm is triggered, which is a significant disadvantage for the authorities who have to search for the wearer starting from his/her last known location.

It is possible to combine the sensors in the setting of overpressure/underpressure/ambient pressure described above for forming different variants of the invention, notably:

- an enclosure 9 essentially at ambient pressure, hermetically sealed relatively to the over-pressurized or under-pressurized channel 8 relatively to ambient pressure, with an ultrasound sensor for the enclosure and a pressure sensor in the channel;
- an over-pressurized or under-pressurized enclosure 9 relative to ambient pressure, hermetically sealed relatively to the channel 8 which is over-pressurized or under-pressurized relatively to ambient pressure, with an ultrasound sensor for the channel and a pressure sensor in the enclosure;
- an over-pressurized or under-pressurized enclosure 9 relatively to ambient pressure, hermetically sealed relatively to the channel 8 essentially to ambient pressure, with an ultrasound sensor for the channel and a pressure sensor in the enclosure;
- an enclosure 9 in fluidic communication with the over-pressurized or under-pressurized channel 8 relative to ambient pressure, with only one or several pressure sensors in the enclosure or in the channel;
- an enclosure 9 in fluidic communication with the over-pressurized or under-pressurized channel 8 relatively to ambient pressure, with one or several pressure sensors in the enclosure or the channel and in addition one or several ultrasound sensors for the channel and/or the enclosure;
- an enclosure 9 in fluidic communication with the over-pressurized or under-pressurized channel 8 relative to ambient pressure, with only one or several ultrasound sensors for the channel and/or the enclosure;
- an enclosure 9 in fluidic communication with the channel 8 essentially at ambient pressure, with only one or several ultrasound sensors for the channel and/or the enclosure.

The circumference of the bracelet, and therefore the length of the channel 8 may vary from one bracelet to another, notably in order to be adapted to the measurements of the wrist or of the ankle of the wearer. The closure system may in this case be adjustable in order to be able to clamp the object up to the desired diameter. Alternatively, casing portions 2*a*, 2*b* of different sizes may be provided.

The calibration of the ultrasound and/or pressure sensor(s) according to embodiments and variants, may be carried out once the bracelet is set into place on the wearer. The calibration procedure may comprise storage in a memory of the electronics, of a sensor signal shortly after its setting into place on the wearer, forming a reference value indicating an entire bracelet. Predetermined value thresholds may be set for this signal in order to ensure that the calibration is accomplished on an entire bracelet, notably that the setting into place and the closing of the bracelet are correct, by comparing the reference value after the calibration with predetermined threshold values which take into account possible variations in the geometry of the bracelet, but which set aside integrity failures outside these measurements or these authorized values.

Referring to FIGS. 4*a* to 4*c* and 6*a*, 8*a* to 8*c*, in embodiments, a kit for the monitoring bracelet may advantageously comprise a recharging unit 28 forming an external source of energy, and configured so as to be coupled with the bracelet 1 in order to recharge the internal source of energy 12. The electric coupling between the recharging unit 28 and the bracelet may be accomplished by means of electric terminals 29, 29*a*, 29*b* or either may be a coupling by induction without any direct electric contact. In an advantageous embodiment, the recharging unit 28 is in the form of a portable rechargeable battery, provided with attachment means 30, for example in the form of elastic arms with lugs 31 at their free ends forming elastic clamps which are clipped on either side of a section of the bracelet 1 on protuberances 70*a*, as illustrated in FIG. 8A, and where the grooves of the guide 70*b* (see FIG. 6*a*) assist in positioning the recharging unit. The wearer of the bracelet may therefore move freely during the time for recharging the internal source of energy, unlike the conventional system where recharging is carried out by means of an electric cable attached on the monitoring bracelet. At the end of the recharge process, the recharging unit is freed from the bracelet The batteries of the recharging unit 28 may be recharged by means of a base station or a recharging station 32 as illustrated in FIG. 4*c*, connected to the electric network.

The invention claimed is:

1. An electronic monitoring bracelet for monitoring a person subject to judicial oversight, comprising:

- a ring-shaped body configured for mounting and securely locking around a limb of a person in a manner not unlockable by said person wearing the electronic monitoring bracelet, the ring-shaped body comprising first and second body portions;
- an electronic monitoring system positioned in the body, the electronic monitoring system comprising an integrity detection system including at least one sensor configured for detecting violation of an integrity of the bracelet, and an internal source of energy; and a closing system configured for a reversible locking, the closing system comprising an electromagnet mounted in the first body portion of the ring-shaped body, comprising a coil and one or two pins slidably mounted in a cavity in the center of the electromagnet and biased each by a compression spring in a closed position where they are inserted in a complementary cavity in an extension of the second body portion of the ring-shaped body, wherein the ring-shaped body is in a form of a rigid shell containing a chamber or several chamber sections therein in which components of the electronic monitoring system are positioned, the ring-shaped body in the form of a rigid shell entirely encircling the bracelet and configured to entirely encircle said limb.

2. The bracelet to claim 1, wherein the first and second body portions of the ring-shaped body are formed with two removably rigid coupled portions configured for mounting around a limb and locking together.

3. The bracelet according to claim 1, wherein the compression springs press against a core situated in a center of the coil, the displacement of each pin being limited towards the exterior by a shoulder formed on the pin engaging a stop in a non-magnetic material in the housing of the closing system.

4. The bracelet according to claim 1, wherein the pins are provided with grooves calibrated to rupture on application of a force superior to a pre-determined value.

5. The bracelet according to claim 1, wherein the monitoring system further comprises a localization system, and a communications system for transmitting monitoring and integrity data, and components for forming the integrity detection system and a source of energy, the localization system and the communications system are positioned in several areas distributed around the bracelet in the body.

6. The bracelet according to claim 1, wherein the integrity detection system comprises at least one enclosure and at least one channel positioned in the body, the channel and the enclosure entirely encircling the bracelet and further comprising at least one sensor configured for detecting violation to an integrity of the channel of the enclosure.

7. The bracelet according to claim 6, wherein the monitoring system comprises an electronic card positioned in the enclosure.

8. The bracelet according to claim 6, wherein the channel and/or the enclosure contain(s) a fluid.

9. The bracelet according to claim 1, wherein the chamber or several chamber sections of the rigid shell contain(s) a fluid.

10. The bracelet according to claim 8, wherein the fluid is an under-pressurized or over-pressurized gas relatively to atmospheric pressure.

11. The bracelet according to claim 1, wherein the integrity detection system comprises at least one sensor configured for detecting violation to the integrity of the rigid shell of the ring-shaped body.

12. The bracelet according to claim 11, wherein said at least one sensor comprises a pressure sensor and/or an ultrasound sensor.

13. The bracelet according to claim 1, wherein the chamber or several chamber sections contain a fluid and in that integrity detection system comprises at least one sensor configured for detecting violation to the integrity of the rigid shell of the ring-shaped body.

14. The bracelet according to claim 13, wherein the fluid is a gas at under pressure or over pressure relative to atmospheric pressure.

15. The bracelet according to claim 13, wherein the at least one sensor comprises a pressure sensor configured for measuring a variation of pressure of the fluid.

16. An electronic monitoring bracelet, comprising:

a ring-shaped body configured for mounting around a limb or an object, the ring-shaped body comprising first and second body portions;

an electronic monitoring system positioned in the body, the electronic monitoring system comprising an integrity detection system and an internal source of energy;

a localization system, wherein the integrity detection system comprises at least one enclosure and at least one channel positioned in the body, the channel and the enclosure entirely encircling the bracelet;

at least one sensor configured for detecting violation of an integrity of the channel of the enclosure; and a closing system configured for a reversible locking, the closing system comprising an electromagnet mounted in the first body portion of the ring-shaped body, comprising a coil and one or two pins slidably mounted in a cavity in the center of the electromagnet and biased each by a compression spring in a closed position where they are inserted in a complementary cavity in an extension of the second body portion of the ring-shaped body.

17. The bracelet according to claim 16, wherein said at least one sensor comprises an ultrasound sensor.

18. The bracelet according to claim 17, wherein said at least one ultrasound sensor comprises an ultrasound transmitter and an ultrasound detector arranged at opposing extremities of the channel.

19. The bracelet according to claim 17, wherein said at least one ultrasound sensor comprises at least one ultrasound detector mounted inside the enclosure.

20. The bracelet according to claim 16, wherein the channel contains a fluid.

21. The bracelet according to claim 16, wherein the enclosure contains a fluid.

22. The bracelet according to claim 16, wherein the channel is in fluid communication with the enclosure.

23. The bracelet according to claim 16, wherein the monitoring system comprises an electronic circuit board arranged in the enclosure.

24. The bracelet according to claim 16, wherein the monitoring system comprises a communication system for the transmission of monitoring and integrity data, the communication system comprising a transmitter configured for the transmission of data over a mobile phone network.

25. The bracelet according to claim 16, wherein the localization system comprises a satellite positioning sensor.

26. The bracelet according to claim 16, wherein the first and second body portions of the ring-shaped body are formed of two removably rigid coupled parts configured for mounting and locking together around a limb.

27. A monitoring kit comprising:

an electronic monitoring bracelet comprising:

a ring-shaped body configured for mounting around a limb or an object, the ring-shaped body comprising first and second body portions, an electronic monitoring system positioned in the body, the electronic monitoring system comprising an integrity detection system and an internal source of energy, and a closing system configured for a reversible locking, the closing system comprising an electromagnet mounted in the first body portion of the ring-shaped body, comprising a coil and one or two pins slidably mounted in a cavity in the center of the electromagnet and biased each by a compression spring in a closed position where they are inserted in a complementary cavity in an extension of the second body portion of the ring-shaped body;

a recharging unit comprising one or more rechargeable batteries; and a recharging station independent of the recharging unit and configured to be connected by wire to an electricity network, the recharging unit being configured for mechanically coupling in a removable way with the monitoring bracelet in order to perform wireless recharging of the internal source of energy on the one hand, and on the other hand the recharging unit is configured for connection to the recharging station for recharging the batteries of the recharging unit while the recharging unit is not coupled to the bracelet.

28. The monitoring kit according to claim 27, wherein the ring-shaped body of the monitoring bracelet is in the form of a rigid shell containing a chamber or several chamber sections in which components of the electronic monitoring system are positioned, the ring-shaped body in the form of a rigid shell entirely encircling the bracelet.

29. The monitoring kit according to claim 27, wherein the integrity detection system comprises at least one enclosure and at least one channel positioned in the body, the channel and the enclosure entirely encircling the bracelet, and at least one sensor configured for detecting violation of an integrity of the channel or of the enclosure.

30. The monitoring kit according to claim 29, wherein said at least one sensor comprises a pressure sensor and/or an ultrasound sensor.

31. The monitoring kit according to claim 27, further comprising a localization system including a satellite positioning sensor.

32. The monitoring kit according to claim 27, wherein the monitoring system further comprises a localization system and a communications system for transmitting monitoring and integrity data, and in that components for forming the integrity detection system and the source of energy, the localization system and the communications system are positioned in several areas distributed around the bracelet in the body.

33. The bracelet according to claim 1 or 16, further comprising locking elements, wherein the rigid shell comprises two rigid portions configured to joint together to form at least one locking interface at which both rigid portions are securely locked to each other by the locking elements.

34. The bracelet according to claim 1 or 16, wherein the rigid shell is unbendable.

* * * * *